(12) United States Patent
Tiedtke et al.

(10) Patent No.: US 9,079,042 B2
(45) Date of Patent: Jul. 14, 2015

(54) POWER SUPPLY FOR A RETINA IMPLANT

(75) Inventors: Hans-Jürgen Tiedtke, Bonn (DE); Alexander Rath, Hürtgenwald-Gey (DE)

(73) Assignee: PIXIUM VISION SA, Paris (FR)

( * ) Notice: Subject to any disclaimer, the term of this patent is extended or adjusted under 35 U.S.C. 154(b) by 400 days.

(21) Appl. No.: 12/921,728

(22) PCT Filed: Mar. 20, 2008

(86) PCT No.: PCT/EP2008/002276
§ 371 (c)(1),
(2), (4) Date: Nov. 23, 2010

(87) PCT Pub. No.: WO2009/115102
PCT Pub. Date: Sep. 24, 2009

(65) Prior Publication Data
US 2011/0060410 A1    Mar. 10, 2011

(51) Int. Cl.
*A61F 9/08* (2006.01)
*A61N 1/378* (2006.01)
*A61N 1/36* (2006.01)

(52) U.S. Cl.
CPC .......... *A61N 1/3787* (2013.01); *A61N 1/36046* (2013.01); *A61F 9/08* (2013.01)

(58) Field of Classification Search
CPC ........... A61F 9/08; A61F 9/0727; A61F 2/14; A61F 2230/0091; A61F 2250/0001; A61F 2250/0002; A61F 2310/00011–2310/00155; A61N 1/0543; A61N 1/36046
USPC .......................... 623/6.63, 4.1; 607/53–54, 61
See application file for complete search history.

(56) References Cited

U.S. PATENT DOCUMENTS

| | | | |
|---|---|---|---|
| 3,449,768 A | 6/1969 | Doyle | |
| 3,727,616 A * | 4/1973 | Lenzkes | 607/59 |
| 4,816,758 A * | 3/1989 | Theissen et al. | 324/204 |
| 5,935,155 A | 8/1999 | Humayun | |
| 6,058,330 A * | 5/2000 | Borza | 607/61 |
| 6,400,989 B1 * | 6/2002 | Eckmiller | 607/54 |
| 6,430,444 B1 * | 8/2002 | Borza | 607/61 |
| 6,591,139 B2 * | 7/2003 | Loftin et al. | 607/60 |
| 7,447,548 B2 * | 11/2008 | Eckmiller | 607/54 |
| 7,800,368 B2 * | 9/2010 | Vaughan et al. | 324/318 |
| 8,010,205 B2 * | 8/2011 | Rahman et al. | 607/60 |
| 2003/0093132 A1 * | 5/2003 | Eckmiller | 607/54 |

(Continued)

FOREIGN PATENT DOCUMENTS

| | | |
|---|---|---|
| AU | 2006202503 | 7/2006 |
| CA | 2611851 | 1/2007 |

(Continued)

*Primary Examiner* — Paul Prebilic
(74) *Attorney, Agent, or Firm* — Workman Nydegger

(57) ABSTRACT

A power supply for a retina implant at least partly located in the interior of a patient's eye is described. The power supply comprises a first transmission coil (4, 23), a second transmission coil (5, 24). The power supply further comprises a signal generation unit adapted for generating a first high frequency signal and a second high frequency signal, and for applying the first high frequency signal to the first transmission coil and the second high frequency signal to the second transmission coil, the second high frequency signal being phase shifted relative to the first high frequency signal. The first transmission coil is adapted for transmitting the first high frequency signal, and the second transmission coil is adapted for transmitting the second high frequency signal.

29 Claims, 4 Drawing Sheets

(56) References Cited

U.S. PATENT DOCUMENTS

| | | | |
|---|---|---|---|
| 2003/0149458 A1* | 8/2003 | Williamson et al. | 607/54 |
| 2003/0158588 A1* | 8/2003 | Rizzo et al. | 607/54 |
| 2004/0117011 A1 | 6/2004 | Aharoni et al. | |
| 2005/0021104 A1* | 1/2005 | DiLorenzo | 607/45 |
| 2005/0131495 A1* | 6/2005 | Parramon et al. | 607/61 |
| 2005/0288734 A1* | 12/2005 | Greenberg et al. | 607/54 |
| 2006/0036296 A1* | 2/2006 | Greenberg et al. | 607/54 |
| 2006/0064141 A1* | 3/2006 | Shodo | 607/54 |
| 2007/0225775 A1* | 9/2007 | Tano et al. | 607/54 |
| 2008/0082147 A1* | 4/2008 | Dai et al. | 607/61 |
| 2008/0262611 A1* | 10/2008 | Li et al. | 623/6.63 |
| 2009/0069869 A1* | 3/2009 | Stouffer et al. | 607/61 |

FOREIGN PATENT DOCUMENTS

| | | |
|---|---|---|
| JP | 2005-354197 | 12/2005 |
| JP | 2006-297110 | 11/2006 |
| JP | 2007190064 | 8/2007 |
| JP | 2007208935 | 8/2007 |
| WO | WO 99/45870 | 9/1999 |
| WO | WO00/41125 | 7/2000 |
| WO | WO 00/56393 | 9/2000 |
| WO | 03061537 | 7/2003 |
| WO | WO 2005/029637 | 3/2005 |

* cited by examiner

POWER SUPPLY FOR A RETINA IMPLANT

CROSS-REFERENCE TO RELATED APPLICATIONS

This application is a U.S. Nationalization of PCT International Application No. PCT/EP2008/002276 filed 20 Mar. 2008, entitled "POWER SUPPLY FOR A RETINA IMPLANT," which is incorporated herein by reference in its entirety.

The invention relates to a power supply for a retina implant at least partly located in the interior of a patient's eye, and to a visual prosthesis system. The invention further relates to a method for supplying power to a retina implant.

There exist a variety of different diseases of the retina that are caused by a degeneration of the photosensitive cells of the retina. Examples of degenerative diseases are retinitis pigmentosa, macula degeneration or Usher syndrome. As a result of these degenerative diseases, people slowly loose their vision and eventually suffer from complete blindness. A visual prosthesis system comprising a retina implant is a helpful tool for at least partially reestablishing a modest visual perception and a sense of orientation for blind and visually impaired users.

In general, the electrical power required for the retina implant's operation is supplied to the retina implant via a high frequency electromagnetic field. The electromagnetic field may e.g. be generated by a transmission coil that is integrated into an eyeglass frame. The retina implant comprises a receiver coil adapted for receiving the high frequency electromagnetic field, wherein the received high frequency signal supplies the power required for the retina implant's operation.

However, it is difficult to achieve a satisfying energy transfer to the retina implant. The degree of efficiency for transmitting power to the retina implant is quite limited.

It is an object of the patient invention to provide an improved power supply for a retina implant that allows for a more efficient energy transfer.

The object of the invention is solved by a power supply for a retina implant at least partly located in the interior of a patient's eye. The power supply comprises a first transmission coil and a second transmission coil. The power supply further comprises a signal generation unit adapted for generating a first high frequency signal and a second high frequency signal, and for applying the first high frequency signal to the first transmission coil and the second high frequency signal to the second transmission coil, the second high frequency signal being phase shifted relative to the first high frequency signal. The first transmission coil is adapted for transmitting the first high frequency signal, and the second transmission coil is adapted for transmitting the second high frequency signal.

In prior art solutions, one single transmission coil has been used for transmitting an electromagnetic signal from a transmission coil to a receiver coil of the retina implant. However, due to anatomic restrictions, the receiver coil is not arranged in parallel with the transmission coil. Furthermore, the distance between the transmission coil and the receiver coil is generally quite large. As a consequence, the degree of efficiency for the energy transfer from the transmission coil to the receiver coil is generally quite small, e.g. in the range of 1%.

According to embodiments of the present invention, two or more transmission coils are employed, with each of the transmission coils being adapted for transmitting a dedicated high frequency signal. The first transmission coil radiates a first electromagnetic field and the second transmission coil radiates a second electromagnetic field. Thus, a superposed electromagnetic field is generated as a superposition of the respective electromagnetic fields transmitted by the first and the second transmission coil. At the retina implant, the superposed electromagnetic signal is received by the receiver coil, and the received electromagnetic signal provides the energy required for the retina implant's operation.

The superposed electromagnetic signal can be optimized to provide for an improved energy transfer to the retina implant. For example, by varying the relative phase of the second high frequency signal relative to the first high frequency signal, and by varying the respective amplitudes, a superposed electromagnetic signal adapted to the location and to the reception properties of the receiver coil can be generated. Even if the first and the second transmission coil are not in an optimum position relative to the receiver coil, it is possible to generate a superposed electromagnetic signal that matches with the receiving properties of the receiver coil. Thus, the difficulties with regard to positioning the receiver coil relative to the transmission coils are compensated for.

As a consequence, energy transfer to the receiver coil is optimized, and the degree of efficiency for energy transfer to the receiver coil of the retina implant is increased.

According to a preferred embodiment, the first and the second transmission coil are oriented at a predefined angle relative to one another. Further preferably, the first and the second transmission coil are oriented at an angle between 70° and 120° relative to one another. By arranging the two transmission coils in this manner, each of the transmission coils may provide a respective component of the superposed electromagnetic field.

According to a preferred embodiment, the phase shift of the second high frequency signal relative to the first high frequency signal lies in the range between −120° and +120°. The resulting superposed electromagnetic field depends on the phase shift between the first high frequency signal and the second high frequency signal. For example, by varying the phase shift between the first and the second high frequency signal, the resulting superposed electromagnetic field may be adapted to the location and orientation of the receiver coil.

According to a preferred embodiment, the frequency of the first high frequency signal is substantially equal to the frequency of the second high frequency signal.

According to a preferred embodiment, the frequency of the first high frequency signal and the second high frequency signal is in the range between 100 kHz and 100 MHz. Preferably, high frequency signals in the radio frequency range are preferably used for transferring energy to the receiver coil of the retina implant.

According to a preferred embodiment, the signal generation unit comprises a signal generator adapted for generating a high frequency signal, and a phase shifter adapted for converting the high frequency signal into the first high frequency signal and the second high frequency signal, the second high frequency signal being phase shifted relative to the first high frequency signal. According to this embodiment, a common high frequency signal is used as a starting point for generating the first and the second high frequency signal, wherein a relative phase shift between the first and the second high frequency signal is induced by the phase shifter.

According to a preferred embodiment, the power supply further comprises at least one amplifier adapted for amplifying the first high frequency signal and the second high frequency signal before supplying the first and the second high frequency signal to the first and the second transmission coil, respectively.

According to a preferred embodiment, the power supply comprises a first amplifier adapted for amplifying the first high frequency signal and a second amplifier adapted for amplifying the second high frequency signal. When two separate amplifiers are used for amplifying the first and the second high frequency signal, the respective amplitudes of the first and the second high frequency signal can be controlled independently of one another. Thus, orientation and magnitude of the resulting superposed electromagnetic field can be adjusted by varying the respective amplitudes of the first and the second high frequency signal. The resulting superposed electromagnetic field may e.g. be adapted to the location and orientation of the receiver coil.

According to a preferred embodiment, the power supply further comprises further transmission coils, wherein the signal generation unit is adapted for generating, in addition to the first and the second high frequency signal, further high frequency signals, and for applying the further high frequency signals to the further transmission coils. By providing a set of three or more transmission coils, a more powerful superposed electromagnetic field may be generated. Preferably, by coordinating the amplitudes and phase relations of the various high frequency signals supplied to the transmission coils, an optimum superposition of the various signal components can be accomplished.

According to a preferred embodiment, the power supply further comprises an eyeglass frame, with both the first transmission coil and the second transmission coil being integrated in the eyeglass frame. When the patient wears the eyeglass frame, the first and the second transmission coil are automatically brought to respective predefined positions relative to the retina implant.

According to a preferred embodiment, the first transmission coil is arranged around one of the eyeglasses of the eyeglass frame. According to a further preferred embodiment, the second transmission coil is integrated into one of the temples of the eyeglass frame. When both the first and the second transmission coil are integrated in the eyeglass frame in this manner, the first transmission coil is oriented at an angle of about 70° to 120° relative to the second transmission coil. Accordingly, a superposed electromagnetic field of high strength and adjustability is generated.

A visual prosthesis system according to embodiments of the present invention comprises a power supply as described above, and a retina implant at least partly located in the interior of a patient's eye, the retina implant comprising a receiver coil. The receiver coil is adapted for receiving a superposed high frequency signal transmitted by the first transmission coil and the second transmission coil.

According to a preferred embodiment, the superposed high frequency signal comprises a first signal component transmitted by the first transmission coil and a second signal component transmitted by the second transmission coil. The signal components transmitted by the first and the second transmission coil add up to an overall signal According to a preferred embodiment, the first high frequency signal and the second high frequency signal are operative to transmit electrical power to the retina implant. The first and the second high frequency signal can be adjusted such that the resulting superposed signal matches with the orientation and position of the receiver coil. By adjusting the superposed electromagnetic field to the receiver coil, the degree of efficiency of the energy transfer is improved.

According to a preferred embodiment, the visual prosthesis system further comprises a video camera adapted for acquiring image data and for providing a video signal. In a preferred embodiment, the video camera is integrated into an eyeglass frame.

According to a preferred embodiment, the visual prosthesis system further comprises a data processing unit, the data processing unit being adapted for converting a video signal into corresponding stimulation data for the retina implant.

According to a preferred embodiment, at least one of the first high frequency signal and the second high frequency signal is modulated in accordance with stimulation data to be transmitted to the retina implant. In this embodiment, the first and the second high frequency signals are used both for transferring energy to the retina implant and for transmitting the stimulation data to the retina implant.

According to a preferred embodiment, the retina implant comprises an array of microcontacts adapted for contacting ganglia of the patient's retinal tissue.

According to a preferred embodiment, the retina implant is adapted for receiving stimulation data and for stimulating the micro-contacts according to the stimulation data.

According to a preferred embodiment, the retina implant comprises a stimulation chip adapted for converting stimulation data into corresponding stimulation pulses for the array of micro-contacts. Preferably, the stimulation chip is powered by the electrical energy received by the receiver coil of the retina implant.

Furthermore, a method for supplying power to a retina implant is provided, the retina implant being at least partly located in the interior of a patient's eye. The method comprises generating a first high frequency signal and a second high frequency signal, wherein the second high frequency signal is phase shifted relative to the first high frequency signal, applying the first high frequency signal to a first transmission coil and the second high frequency signal to a second transmission coil, and transmitting the first high frequency signal by the first transmission coil and the second high frequency signal by the second transmission coil.

According to a preferred embodiment, the method further comprises adjusting the phase shift between the first high frequency signal and the second high frequency signal to optimize energy transfer to the retina implant. The phase shift between the first and the second high frequency signal effects the superposed electromagnetic field. Hence, by varying the phase shift, the orientation of the electromagnetic field may be adjusted to the orientation of the receiver coil, and energy transfer to the receiver coil may be optimized.

According to a preferred embodiment, the method further comprises adjusting respective signal amplitudes of the first high frequency signal and the second high frequency signal to optimize energy transfer to the retina implant. By varying the respective amplitudes of the first and the second high frequency signal, it is possible to vary both the orientation and the strength of the resulting electromagnetic field. The orientation of the electromagnetic field may be matched with the orientation of the receiver coil. Thus, energy transfer to the receiver coil may be optimized.

For a better understanding of the present invention and to show how the same be carried into effect, reference will now be made by a way of example to the accompanying drawings in which:

FIG. 1 gives an overview of a visual prosthesis system;

Figure 1:
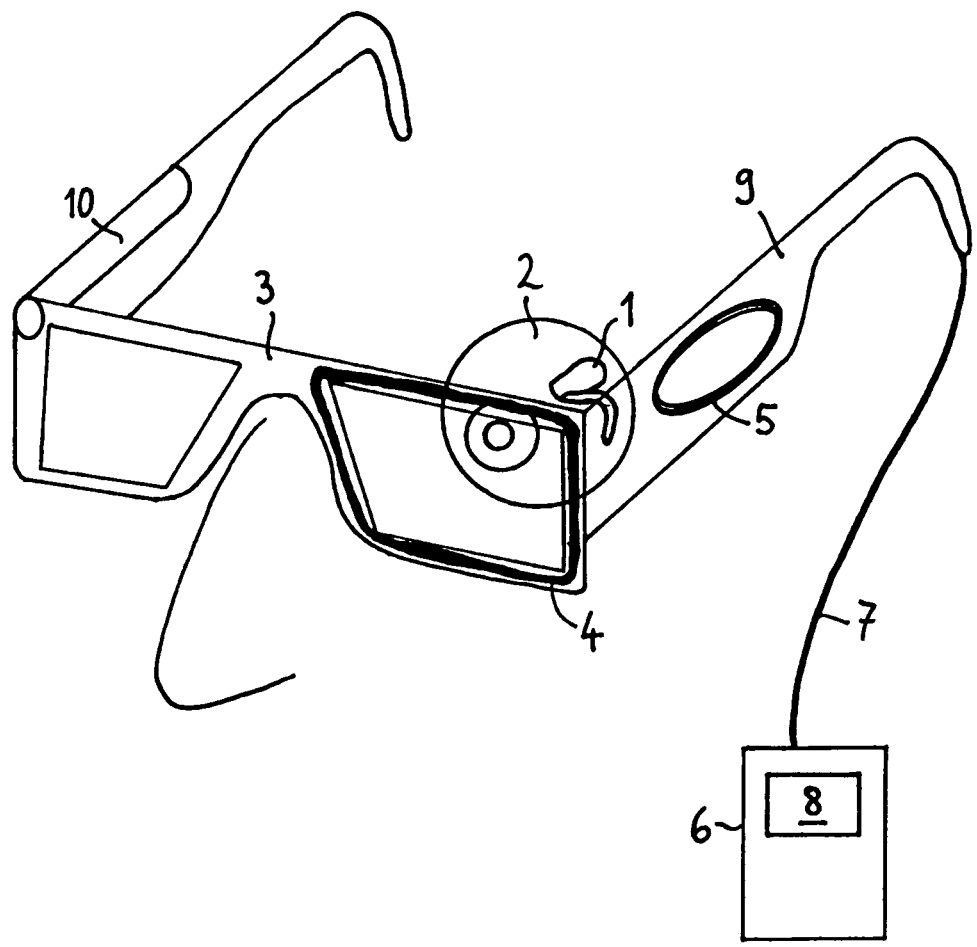

FIG. 1 shows a visual prosthesis system for at least partially reestablishing a modest visual perception and a sense of orientation for blind and visually impaired users. There exist a variety of different diseases of the retina that are caused by a degeneration of the photosensitive cells of the retina. Examples for degenerative diseases are retinitis pigmentosa, macula degeneration or Usher syndrome. As a result of these regenerative diseases, people slowly loose their vision and eventually suffer from complete blindness.

The visual prosthesis system shown in FIG. 1 comprises a retinal implant 1 that may for example comprise an intraocular part located within the eyeball 2 and an extraocular part located at the outer surface of the eyeball 2. The intraocular part of the retinal implant 1 comprises an array of micro-contacts that is in direct contact with the patient's retina, wherein the micro-contacts are adapted for electrically contacting the retinal tissue.

The visual prosthesis system further comprises a visual interface 3, which may for example be realized as an eyeglass frame. The visual interface 3 is adapted for supplying energy to the retina implant 1, and for performing wireless data communication with the retina implant 1. The energy transfer from the visual interface 3 to the retina implant 1 is effected by a first transmission coil 4 and a second transmission coil 5 which are both integrated in the eyeglass frame. The visual prosthesis system comprises a pocket computer 6 that is connected to the visual interface 3 via a wire connection 7. The pocket computer 6 comprises a signal generation unit 8 that generates a first high frequency signal for the first transmission coil 4 and a second high frequency signal for the second transmission coil 5. Preferably, the two high frequency signals have the same frequency, with the frequency of the first and the second high frequency signal being in the range between 100 kHz and 100 MHz. Further preferably, the second high frequency signal is phase shifted relative to the first high frequency signal.

Via the wire connection 7, the first high frequency signal is supplied to the first transmission coil 4, and the second high frequency signal is supplied to the second transmission coil 5. The first transmission coil 4 transmits the first high frequency signal, and the second transmission coil 5 transmits the second high frequency signal. The first and the second transmission coil 4, 5 radiate an electromagnetic field having a frequency in the radio frequency range.

Preferably, the first transmission coil 4 is arranged at an angle between 70° and 120° relative to the second transmission coil 5. For example, the first transmission coil 4 may be arranged around one of the eyeglasses of the eyeglass frame, whereas the second transmission coil 5 may be integrated into one of the temples 9 of the eyeglass frame.

The retina implant 1 comprises a receiver coil for receiving the superposed electromagnetic field generated by the first transmission coil 4 and the second transmission coil 5. The electromagnetic signal received by the receiver coil provides the electrical power for operation of the retina implant 1.

The visual interface 3 may further comprise a video camera 10 for acquiring a video image of the patient's field of view. Video signals acquired by the video camera 10 are transmitted to the pocket computer 6. There, the video signals are converted into corresponding stimulation data for the array of micro-contacts on the retina implant 1. The stimulation data determined by the pocket computer 7 is forwarded to the visual interface 3 and transmitted to the retina implant 1.

For transmitting the stimulation data to the retina implant 1, there exist different alternatives. According to a first embodiment, the stimulation data is modulated onto at least one of the first and the second high frequency signal. At the retina implant, the received electromagnetic signal is demodulated. In this embodiment, the first and the second high frequency signal are used both for data communication and for transferring energy to the retina implant 1.

According to a second embodiment, the stimulation data is transmitted to the retina implant 1 via a modulated light beam, preferably via modulated infrared light. In this embodiment, the first and the second high frequency signals are solely used for transferring energy to the retina implant 1.

At the retina implant 1, the stimulation data is decoded. In accordance with the stimulation data, stimulation pulses are applied to the micro-contacts of the retina implant 1. The stimulation of the retinal tissue causes a visual impression.

Figure 2:
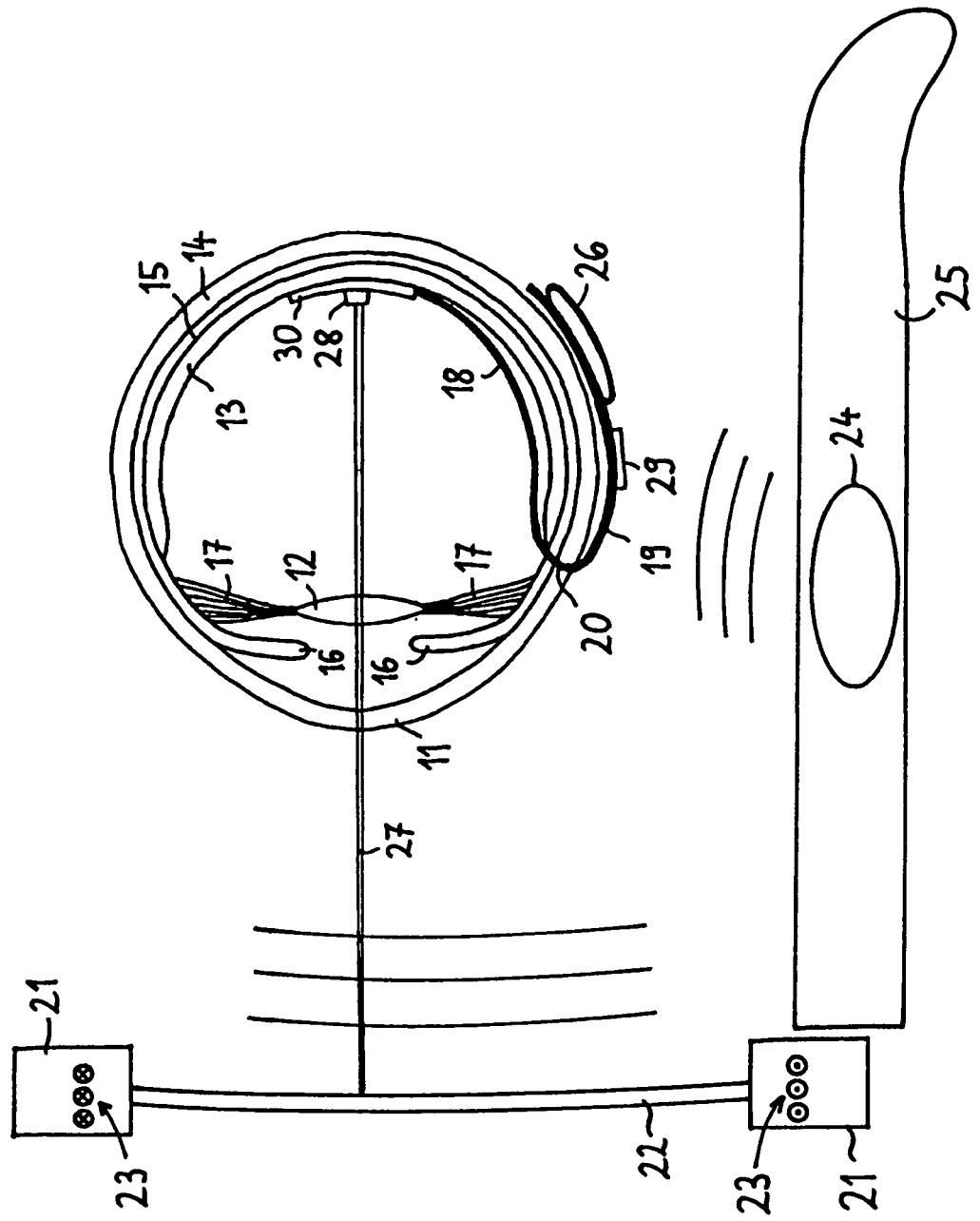
FIG. 2 shows a cross section of an eyeball comprising a retina implant.

FIG. 2 shows a cross section of a patient's eye comprising a retinal implant. External light passes the cornea 11 and the eye lens 12 and strikes the retina 13. The retina 13 covers a large part of the eyeball's interior. The eyeball's outer surface is formed by the sclera 14. Between the retina 13 and the sclera 14, a choroid membrane 15 is located. The iris 16 determines the amount of light that may enter into the interior of the eye. The eye lens 12 is fixed by the ciliary muscle 17.

The retina implant comprises an intraocular part 18 and an extraocular part 19. The intraocular part 18 is located in the interior of the eye, whereas the extraocular part 19 is fixed to the outer surface of the sclera 14. The intraocular part 18 and the extraocular part 19 are electrically connected by wire connections 20 that pass through the sclera 14 at a position right behind the ciliary muscle 17.

The patient wears an eyeglass frame 21 with glasses 22. A first transmission coil 23 is arranged around one of the eyeglasses. A second transmission coil 24 is integrated in one of the temples 25 of the eyeglass frame 21. The first transmission coil 23 is adapted for transmitting a first high frequency signal, and the second transmission coil 24 is adapted for transmitting a second high frequency signal. The electromagnetic field generated by the first transmission coil 23 is superposed with the electromagnetic field generated by the second transmission coil 24. The extraocular part 19 of the retina implant comprises a receiver coil 26, the receiver coil 26 being adapted for receiving the superposed electromagnetic signal and for supplying electrical power to the components of the retina implant. Energy transfer from the first and the second transmission coil 23, 24 to the receiver coil 26 can be optimized by adjusting the relative phases and the respective amplitudes of the first and the second high frequency signal. Thus, the superposed electromagnetic field can be adjusted to the orientation of the receiver coil 26.

Additionally, stimulation data carrying visual information has to be transmitted from the visual interface to the retina implant. In the embodiment depicted in FIG. 2, a modulated infrared beam 27 is used for transmitting the stimulation data to the retina implant. The infrared beam 27 may for example be generated by an infrared transmitter LED located in the vicinity of the glasses 22. The modulated infrared beam 27 passes through the eye lens 12 and strikes an optical receiver element 28 (e.g. a photodiode) located on the intraocular part 18 of the retina implant. The stimulation data received by the optical receiver element 28 is forwarded via the wire connection 20 to a retina stimulation chip 29 located on the extraocular part 18 of the retina implant. Preferably, the retina stimulation chip 29 is implemented as a digital signal processing chip. The retina stimulation chip 29 is operative to convert the stimulation data into corresponding stimulation pulses for an array 30 of micro-contacts located directly on the retina 13. The stimulation pulses are supplied to the array 30 of micro-contacts via the wire connection 20. The micro-contacts are adapted for stimulating the ganglia of the retina 13, and this stimulation causes a visual impression.

According to an alternative embodiment, instead of transmitting the stimulation data to the retina implant via a modulated infrared beam 27, the stimulation data may be modulated onto at least one of the first and the second high frequency signal. According to this embodiment, the first and the second high frequency signal are adapted both for transferring energy and for transmitting the stimulation data to the retina implant.

Figure 3:
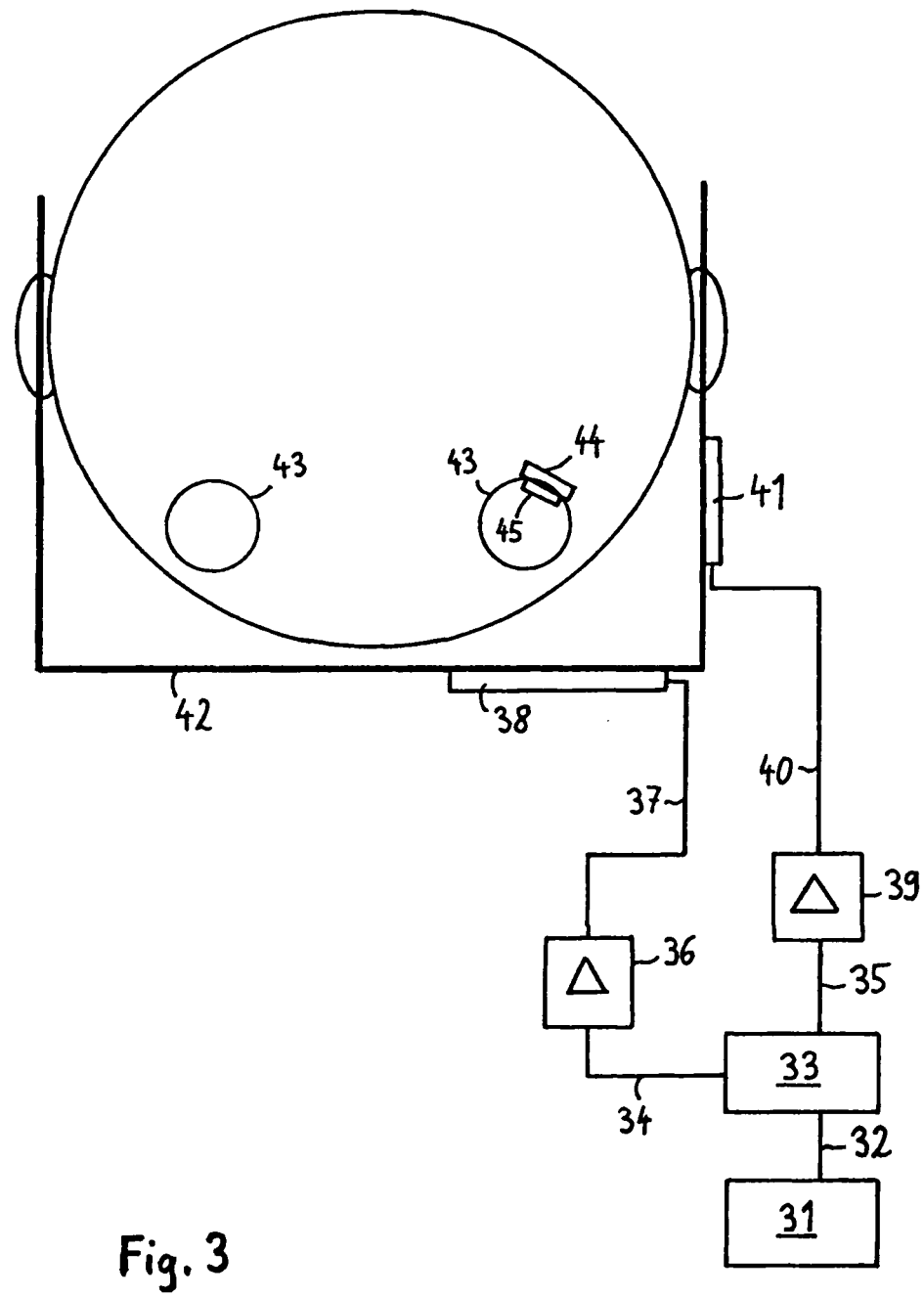
FIG. 3 shows the circuitry for generating high frequency signals for the respective transmission coils.

FIG. 3 shows the circuitry for generating the first and the second high frequency signal. A signal generator 31 provides a high frequency signal 32 to a phase shifter 33, and the phase shifter 33 converts the high frequency signal 32 into a first high frequency signal 34 and a second high frequency signal 35. The phase shifter 33 induces a relative phase shift between the first high frequency signal 34 and the second high frequency signal 35. Preferably, the phase shift is in the range between −120° and +120°. The first high frequency signal 34 is amplified by a first amplifier 36, and the amplified first high frequency signal 37 is supplied to a first transmission coil 38. Accordingly, the second high frequency signal 35 is amplified by a second amplifier 39, and the amplified second high frequency signal 40 is supplied to a second transmission coil 41. Both the first transmission coil 38 and the second transmission coil 41 are integrated into an eyeglass frame 42.

A retina implant 44 with a receiver coil 45 has been attached to one of the patient's eye-balls 43. The receiver coil 45 receives a superposed electromagnetic signal comprising a component transmitted by the first transmission coil 38 and a component transmitted by the second transmission coil 41.

Figure 4:
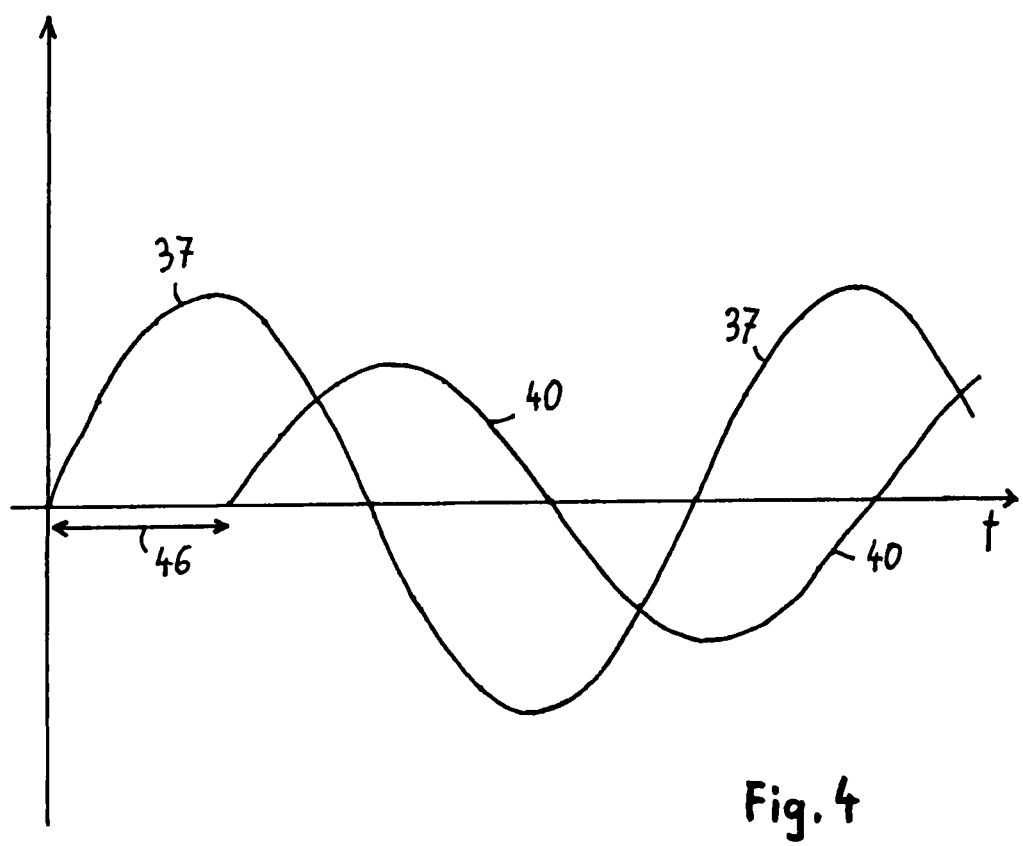
FIG. 4 shows a phase shift between the amplified first high frequency signal and the amplified second high frequency signal.

In FIG. 4, the amplified first high frequency signal 37 and the amplified second high frequency signal 40 are shown as a function of time. Both signals have the same frequency. The amplitude of the amplified first high frequency signal 37 is determined by the gain of the first amplifier 36, whereas the amplitude of the amplified second high frequency signal 40 is determined by the gain of the second amplifier 39. Hence, the two amplitudes may be varied independently. The amplified second high frequency signal 40 is phase shifted relative to the amplified first high frequency signal 37, with the phase shift 46 being induced by the phase shifter 33. By varying the amplitudes of the amplified first and second high frequency signal 37 and 40, and by varying the relative phase shift 46 between the amplified first high frequency signal 37 and the amplified second high frequency signal 40, the resulting superposed electromagnetic field can be adjusted to the location and orientation of the receiver coil 45 in a way that the energy transfer from the first and second transmission coil 38 and 41 to the receiver coil 45 is optimized, thus improving the degree of efficiency of energy transfer from the first and the second transmission coil 38 and 41 to the retina implant.

The invention claimed is:

1. A power supply for a retina implant adapted to be at least partly located in the interior of a patient's eye, the power supply comprising a first transmission coil;
a second transmission coil;
a signal generation unit adapted for generating a high frequency signal;
a phase shifter configured to convert the high frequency signal generated by the signal generation unit into a first high frequency signal that is applied to the first transmission coil and a second high frequency signal that is applied to the second transmission coil, wherein the phase shifter is configured to shift a phase of the first high frequency signal relative to the second high frequency signal;
wherein the first transmission coil is adapted for transmitting the first high frequency signal to a receiver coil, and wherein the second transmission coil is adapted for transmitting the second high frequency signal to the receiver coil,
wherein the first high frequency signal and the second high frequency signal are configured for creating a superposed high frequency signal for the receiver coil, each of the transmission coils being configured for providing a respective component of the superposed high frequency signal,
wherein the phase shifter adjusts the phase shift in order to adapt a superposed electromagnetic field of the superposed signal to an orientation of the receiver coil, and
wherein a frequency of the first high frequency signal is equal to the frequency of the second high frequency signal.

2. The power supply of claim 1, further comprising at least one of:
the first and the second transmission coil are oriented at a predefined angle relative to one another;
the first and the second transmission coil are oriented at an angle between 70° and 120° relative to one another;
the phase shift of the second high frequency signal relative to the first high frequency signal lies in the range between −120° and +120°;
the frequency of the first high frequency signal and the second high frequency signal is in the range between 100 kHz and 100 MHz.

3. The power supply of claim 1, further comprising at least one amplifier adapted for amplifying the first high frequency signal and the second high frequency signal before supplying the first and the second high frequency signal to the first and the second transmission coil, respectively.

4. The power supply of claim 1, comprising a first amplifier adapted for amplifying the first high frequency signal and a second amplifier adapted for amplifying the second high frequency signal.

5. The power supply of claim 1, further comprising further transmission coils, wherein the signal generation unit is adapted for generating, in addition to the first and the second high frequency signal, further high frequency signals, and for applying the further high frequency signals to the further transmission coils.

6. The power supply of claim 1, further comprising an eyeglass frame, with both the first transmission coil and the second transmission coil being integrated in the eyeglass frame.

7. The power supply of claim 6, wherein the first transmission coil is arranged around one of the eyeglasses of the eyeglass frame.

8. The power supply of claim 6, wherein the second transmission coil is integrated into one of the temples of the eyeglass frame.

9. A visual prosthesis system comprising
a power supply according to claim 1;
a retina implant adapted to be at least partly located in the interior of a patient's eye, the retina implant comprising the receiver coil;
wherein the receiver coil is adapted for receiving the superposed high frequency signal transmitted by the first transmission coil and the second transmission coil.

10. The visual prosthesis system of claim 9, wherein the superposed high frequency signal comprises a first signal component transmitted by the first transmission coil and a second signal component transmitted by the second transmission coil.

11. The visual prosthesis system of claim 9, wherein the first high frequency signal and the second high frequency signal are operative to transmit electrical power to the retina implant.

12. The visual prosthesis system of claim 9, further comprising a video camera adapted for acquiring image data and for providing a video signal.

13. The visual prosthesis system of claim 12, wherein the video camera is integrated into an eyeglass frame.

14. The visual prosthesis system of claim 9, further comprising a data processing unit, the data processing unit being adapted for converting a video signal into corresponding stimulation data for the retina implant.

15. The visual prosthesis system of claim 9, wherein at least one of the first high frequency signal and the second high frequency signal is modulated in accordance with stimulation data to be transmitted to the retina implant.

16. The visual prosthesis system of claim 9, wherein the retina implant further comprises an array of micro-contacts adapted for contacting ganglia of the patient's retinal tissue.

17. The visual prosthesis system of claim 16, wherein the retina implant is adapted for receiving stimulation data and for stimulating the micro-contacts according to the stimulation data.

18. The visual prosthesis system of claim 16, wherein the retina implant further comprises a stimulation chip adapted for converting stimulation data into corresponding stimulation pulses for the array of micro-contacts.

19. A method for supplying power to a retina implant at least partly located in the interior of a patient's eye, the method comprising
generating a first high frequency signal and a second high frequency signal, wherein the second high frequency signal is phase shifted relative to the first high frequency signal,
applying the first high frequency signal to a first transmission coil and the second high frequency signal to a second transmission coil,
transmitting the first high frequency signal by the first transmission coil and the second high frequency signal by the second transmission coil, wherein a frequency of the first high frequency signal is equal to the frequency of the second high frequency signal, wherein the first high frequency signal and the second high frequency signal are configured for creating a superposed high frequency signal for a receiver coil, each of the transmission coils being configured for providing a respective component of the superposed signal, and
controlling the phase shift between the first high frequency signal and the second high frequency signal such that a superposed electromagnetic field of the superposed signal is adjusted to an orientation of the receive coil.

20. The method of claim 19, further comprising receiving the superposed high frequency signal at the receiver coil of the retina implant.

21. The method of claim 19, wherein the superposed high frequency signal comprises a first signal component transmitted by the first transmission coil and a second signal component transmitted by the second transmission coil.

22. The method of claim 19, wherein generating a first high frequency signal and a second high frequency signal comprises
generating a high frequency signal,
converting the high frequency signal into a first high frequency signal and a second high frequency signal, wherein the second high frequency signal is phase shifted relative to the first high frequency signal.

23. The method of claim 19, further comprising
generating, in addition to the first and the second high frequency signal, further high frequency signals,
applying the further high frequency signals to further transmission coils.

24. The method of claim 19, further comprising modulating at least one of the first high frequency signal and the second high frequency signal in accordance with stimulation data to be transmitted to the retina implant.

25. The method of claim 19, further comprising
adjusting the phase shift between the first high frequency signal and the second high frequency signal to optimize energy transfer to the retina implant.

26. The method of claim 19, further comprising
adjusting respective signal amplitudes of the first high frequency signal and the second high frequency signal to optimize energy transfer to the retina implant.

27. A power supply for a retina implant adapted to be at least partly located in the interior of a patient's eye, the power supply comprising
a first transmission coil;
a second transmission coil;
a signal generation unit adapted for generating a first high frequency signal and a second high frequency signal, and for applying the first high frequency signal to the first transmission coil and the second high frequency signal to the second transmission coil, the second high frequency signal being phase shifted relative to the first high frequency signal;
wherein the first transmission coil is adapted for transmitting the first high frequency signal, and wherein the second transmission coil is adapted for transmitting the second high frequency signal and wherein a frequency of the first high frequency signal is equal to the frequency of the second high frequency signal,
wherein the first high frequency signal and the second high frequency signal are configured for creating a superposed high frequency signal for a receiver coil, each of the transmission coils being configured for providing a respective component of the superposed signal,
wherein at least one of:
the first and the second transmission coil are oriented at a predefined angle relative to one another,
the first and the second transmission coil are oriented at an angle between 70° and 120° relative to one another,
the signal generation unit is capable of generating a phase shift of the second high frequency signal relative to the first high frequency signal that lies in the range between −120° and +120° and is controlled-such that a superposed electromagnetic field of the superposed signal is adjusted to an orientation of the receiver coil, or
the signal generation unit is capable of generating a frequency of the first high frequency signal and the second high frequency signal in the range between 100 kHz and 100 MHz.

28. A power supply for a retina implant adapted to be at least partly located in the interior of a patient's eye, the power supply comprising
a first transmission coil;
a second transmission coil;
a signal generation unit adapted for generating a first high frequency signal and a second high frequency signal, and for applying the first high frequency signal to the first transmission coil and the second high frequency signal to the second transmission coil, the second high frequency signal being phase shifted relative to the first high frequency signal;

wherein the first transmission coil is adapted for transmitting the first high frequency signal to a receiver coil, and wherein the second transmission coil is adapted for transmitting the second high frequency signal to the receiver coil, wherein the first high frequency signal and the second high frequency signal are configured for creating a superposed signal for the receiver coil, each of the transmission coils being configured for providing a respective component of the superposed signal wherein the phase shift between the first high frequency signal and the second high frequency signal is adjusted such that a resulting electromagnetic field of the superposed signal is adjusted to a location and orientation of the receiver coil so as to optimize energy transfer from the first and second transmission coil to the receiver coil, and wherein a frequency of the first high frequency signal is equal to the frequency of the second high frequency signal.

29. A power supply for a retina implant adapted to be at least partly located in the interior of a patient's eye, the power supply comprising a first transmission coil;

a second transmission coil;

a signal generation unit adapted for generating a first high frequency signal and a second high frequency signal;

a phase shifter configured to shift a phase of the second high frequency signal relative to the first high frequency signal;

wherein the first transmission coil is adapted for transmitting the first high frequency signal to a receiver coil, and wherein the second transmission coil is adapted for transmitting the second high frequency signal to the receiver coil, wherein the first high frequency signal and the second high frequency signal are configured for creating a superposed high frequency signal for the receiver coil, each of the transmission coils being configured for providing a respective component of the superposed signal, wherein the phase shifter is configured to control the shifted phase such that a superposed electromagnetic field of the superposed signal is adjusted to an orientation of the receiver coil to optimize signal transfer to the receiver coil, and wherein a frequency of the first high frequency signal is equal to the frequency of the second high frequency signal.

* * * * *